(12) United States Patent
Akahori

(10) Patent No.: US 7,881,434 B2
(45) Date of Patent: Feb. 1, 2011

(54) RADIOGRAPHIC IMAGING SYSTEM

(75) Inventor: Sadato Akahori, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/458,365

(22) Filed: Jul. 9, 2009

(65) Prior Publication Data

US 2010/0020929 A1  Jan. 28, 2010

(30) Foreign Application Priority Data

Jul. 25, 2008  (JP)  ............................. 2008-192338

(51) Int. Cl.
*H05G 1/64* (2006.01)
(52) U.S. Cl. .................................... 378/98.12; 378/116
(58) Field of Classification Search ......... 378/114–116, 378/62, 98, 98.12, 197
See application file for complete search history.

(56) References Cited

U.S. PATENT DOCUMENTS 7,142,632 B2 * 11/2006 Atzinger et al. ............... 378/62

2004/0188625 A1 * 9/2004 Schulze-Ganzlin .... 250/370.09
2004/0247081 A1   12/2004 Halsmer et al.
2005/0220269 A1 * 10/2005 Endo et al. ................... 378/114

FOREIGN PATENT DOCUMENTS

JP      2005-65940      3/2005

* cited by examiner

*Primary Examiner*—Hoon Song
(74) *Attorney, Agent, or Firm*—Jean C. Edwards, Esq.; Akerman Senterfitt

(57) ABSTRACT

A radiographic imaging system comprises: a radiation source for irradiating an examinee with radiation; a radiation detector for detecting radiation that has penetrated the examinee to acquire radiographic image data; image data receiving unit for receiving the radiographic image data from the radiation detector and outputting a termination signal indicating that an image has been taken each time receiving the radiographic image data; control unit for controlling operations of the radiation source and the radiation detector and detecting a progress of an imaging session for successively taking a series of images according to the termination signal outputted from the image data receiving unit; and progress notification unit for notifying the examinee of a progress of imaging session detected by the control unit.

8 Claims, 2 Drawing Sheets

RADIOGRAPHIC IMAGING SYSTEM

CROSS-REFERENCE TO RELATED APPLICATIONS

The present application claims priority from Japanese Patent Application No. 2008-192338, filed Jul. 25, 2008, the contents of which are herein incorporated by reference in their entirety.

BACKGROUND OF THE INVENTION

The present invention relates to a radiographic imaging system for taking a radiographic image of an examinee and more particularly to a radiographic imaging system whereby the examinee is allowed to know the progress of imaging session as in long region imaging where a series of successive images are taken.

A radiographic image detector has been conventionally used in medicine to produce diagnostic images or in industry to conduct nondestructive tests. The radiographic image detector converts radiation that has penetrated a subject into an electric signal to achieve radiographic imaging. The radiation here includes X-ray, alpha ray, beta ray, gamma ray, electron beam, and ultraviolet ray.

The radiographic image detector is exemplified by a solid state radiation detector, i.e., so-called a flat panel detector hereinafter referred to as FPD, which converts radiation into an electric image signal, and an X-ray image tube that converts a radiographic image into a visible image.

In a radiographic imaging system using an FPD, a subject is irradiated with radiation emitted from a radiation source, whereupon the FPD converts the radiation that has penetrated the subject into an electric signal, and the electric signal corresponding to image data of the subject is read out from the FPD to produce a radiographic image.

To permit appropriate and efficient operations of such a radiographic imaging system, various propositions have been made to allow the operator (medical doctor or radiologist) to know the state of the imaging system and the conditions of the imaging session.

For example, JP 2005-65940 A discloses a radiographic imaging system (X-ray imaging system) comprising an imaging preparation switch and an imaging switch, as well as a hand switch that is removable from an operation panel, wherein the hand switch emits green light upon completion of preparation of the system for imaging in response to depression of the imaging preparation switch and emits orange light upon completion of imaging by the system in response to depression of the imaging switch, thereby notifying the operator of the state of the system and the progress of the imaging session.

US 2005/0220269 A1 discloses a radiographic imaging system provided with two operation periods, one of which is an idle operation period in which a readout interval for idle readout performed to remove a residual image prior to exposure alternates repeatedly with a wait interval during which exposure is possible, the other being a readout period for a post-exposure readout. In this system, immediately after the beginning of the wait period, an exposure guide signal through sound, light, vibration, etc. is generated indicating that exposure is possible to allow the operator to effect exposure at an appropriate timing in the idle operation period.

Such a radiographic imaging system typically performs imaging (normal imaging) such that an image is taken of the examinee, holding still, by a single exposure (irradiation).

Also known is an imaging method, such as long region imaging and tomosynthesis imaging, whereby a plurality of images are successively taken of (or images are successively taken by scanning) an examinee, who is asked to stay motionless, by changing the imaging position (imaging region) or the imaging angle (radiation emission angle).

Long region imaging is an imaging method for taking radiographic images of a long region that is longer than the imaging surface of the FPD such as the whole region of a spine (the whole spine) and the whole region of lower extremities (the whole lower extremities).

Presently, a typical FPD measures only about 43 cm×43 cm. Therefore, a long region such as the whole spine and the whole lower extremities cannot be covered by taking an image thereof only once.

Long region imaging is an imaging method of producing an image of such a long region. As disclosed in US 2004/0247081 A1, the number of times images are taken and the positions in which images are taken are determined according to the imaging region to be covered and the size of the FPD used, and the FPD and the radiation exposure field are moved along the examinee's body axis according to the determined imaging positions to take images (i.e., short images) in different regions a plurality of times, thereby producing an image of a long region covering the whole spine or the whole lower extremities. In long region imaging, short images thus taken are combined to obtain a long radiographic image of the whole spine, the whole lower extremities or the like.

Tomosynthesis imaging is an imaging method whereby a portion under examination is scanned by radiation in such a manner that the angle at which radiation hits the portion under examination is successively changed when carrying out successive imaging to produce a number of projection images, which are used to restructure a radiographic image of a desired tomographic plane.

Naturally, imaging methods as exemplified by long region imaging and tomosynthesis imaging, where a series of images are taken successively, take a longer time than normal imaging.

In addition, the examinee is required to stay motionless until imaging is completed.

In normal imaging, the examinee knows that a given imaging session has been completed when a single image has been taken (by a single exposure). However, in an imaging session such as long region imaging wherein a series of images are successively taken, the examinee is ignorant when the imaging session will end.

In addition, in the conventional radiographic imaging system, while the operator can be aware of the state of the system and the progress of the imaging session, the examinee remains ignorant of the progress of the imaging session.

Thus, in long region imaging, for example, the examinee is left totally ignorant of the time when the imaging session will end, the length of time it will take to complete the imaging session, and the progress of the imaging session and required to stay stationary and wait without being allowed to move until the operator gives an instruction.

Such conditions where the examinee is left ignorant of the length of time it will take to complete the imaging session and of the progress thereof and required to wait motionlessly causes anxiety to and produces psychological burden on the part of the examinee.

In particular, where the examinee is an elderly person or an individual with disabilities or where the examinee has suffered an injury such as a bone fracture, the examinee will feel a significantly great anxiety or psychological burden when he/she is required to hold still patiently even for a short period of time.

SUMMARY OF THE INVENTION

An object of the present invention is to solve the above problems associated with the prior art and provide a radiographic imaging system that allows the examinee (patient) to know the progress of an imaging session, such as a remaining number of images to be taken out of the series of images and a remaining imaging time in the imaging session for taking the series of images, in long region imaging, tomosynthesis imaging, or the like where images of the examinee are successively taken by a radiographic imaging system having functions of successively taking a series of images, thereby reducing a psychological burden or an anxiety on the part of the examinee.

A radiographic imaging system according to the present invention comprises: a radiation source for irradiating an examinee with radiation; a radiation detector for detecting radiation that has penetrated the examinee to acquire radiographic image data; image data receiving means for receiving the radiographic image data from the radiation detector and outputting a termination signal indicating that an image has been taken each time receiving the radiographic image data; control means for controlling operations of the radiation source and the radiation detector and detecting a progress of an imaging session for successively taking a series of images according to the termination signal outputted from the image data receiving means; and progress notification means for notifying the examinee of a progress of imaging session detected by the control means.

DETAILED DESCRIPTION OF THE INVENTION

Now, the radiographic imaging system of the invention will be described in detail referring to a preferred embodiment illustrated in the attached drawings.

Figure 1:
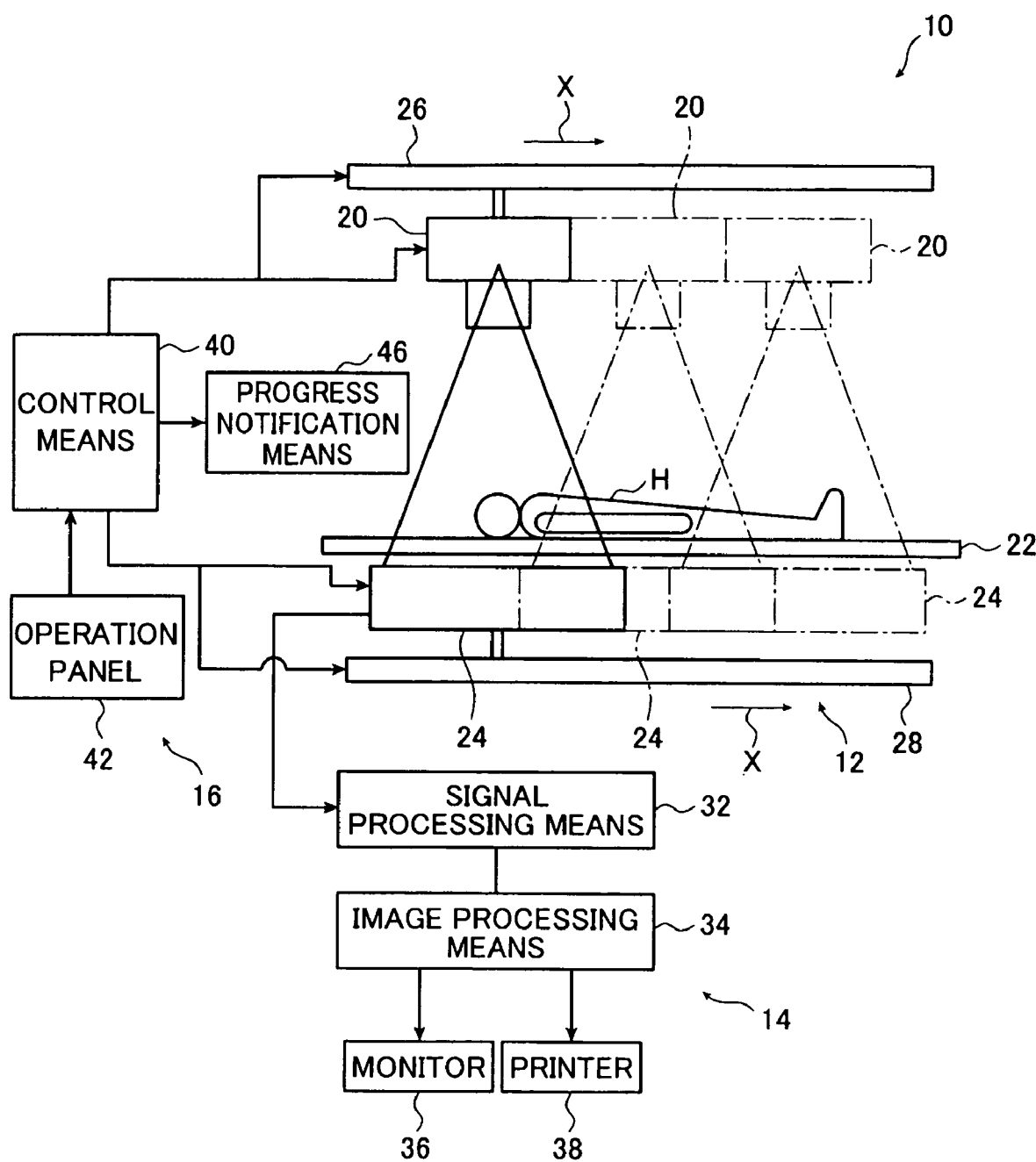
FIG. 1 is a view illustrating a radiographic imaging system according to one embodiment of the invention.

FIG. 1 schematically illustrates a radiographic imaging system 10 according to one embodiment of the invention. The radiographic imaging system 10 causes radiation to penetrate an examinee H, causes a radiation detector 24 to detect the radiation having penetrated the examinee H, and processes image data of a radiographic image thus acquired to produce a radiographic image of the examinee H. The radiographic imaging system 10 comprises an imaging unit 12, data processing/output unit 14 and a control unit 16.

Note that the imaging system 10 is also capable of long region imaging in addition to normal imaging where a radiographic image of the examinee H, asked to stay motionless, is taken by a single exposure. The long region imaging will be described later in detail.

The imaging unit 12 takes a radiographic image of the examinee H and comprises a radiation source 20, an imaging table 22, a radiation detector (referred to as FPD below) 24, a radiation source carrier 26, and a detector carrier 28.

The radiation source 20 is a known radiation source used in various radiographic imaging systems.

The radiation source carrier 26 moves the radiation source 20 in the direction along the body axis of the examinee H lying on the imaging table 22 (lengthwise of the imaging table 22 as indicated by the arrow x in the drawing). In the imaging system 10, the radiation source carrier 26 moves the radiation source 20 to change the radiation exposure field along the body axis of the examinee H in long region imaging.

The radiation source carrier 26 is not limited in any manner and may be any moving means used for radiographic imaging systems that perform long region imaging, such as a gear transmission mechanism as exemplified by a rack and pinion, a screw transmission mechanism, a ball screw transmission mechanism, a wrapping drive mechanism using pulleys, etc., or a method using a cylinder such as an air cylinder or an oil cylinder.

The radiation exposure field in long region imaging may be changed by any method that is not limited to the one illustrated in the drawing where the radiation source 20 is moved in a given direction. The radiation exposure field may be changed by any of various known methods including a method whereby the radiation exposure field is changed by varying the angle of the radiation source 20 (by turning the tube) and a method whereby the radiation exposure field is changed by moving an aperture that is used to restrict the position of the exposure field. Alternatively, instead of changing the radiation exposure field, one may use a radiation source capable of irradiating the whole region to be covered thereby to achieve long region imaging just by moving the radiation detector 24 described later.

The imaging table 22 is provided to allow the examinee H to lie thereon (in a dorsal, ventral, or lateral recumbent position) and locate him/her in a given imaging position.

The imaging table 22 is formed such that a region thereof for taking a radiographic image is formed of a radiotransparent material like any imaging table used in normal radiographic imaging systems.

The FPD 24 is a known radiation (radiographic image) detector that detects and converts radiation that has penetrated the examinee H into an electric signal and outputs an electric signal corresponding to the intensity of the detected radiation.

Accordingly, the FPD 24 may be any one of a direct type FPD whereby radiation is directly converted into an electric charge and an indirect type FPD whereby radiation is temporarily converted into light, which is then converted into an electric signal.

The direct type FPD is configured, for example, of a photoconductive film such as one made of amorphous selenium, a capacitor, a TFT (thin-film transistor) as a switching device, and the like. For example, electron-hole pairs are generated from the photoconductive film upon entry of radiation such as X-ray. The electron-hole pairs are stored in the capacitor, and the electric charge stored in the capacitor is read out through the TFT as an electric signal.

On the other hand, the indirect type FPD is configured, for example, of a scintillator layer formed of a phosphor, a photodiode, a capacitor, a TFT, and the like. The scintillator layer is formed of a phosphor such as "CsI:Tl" that emits light in response to incoming light such as radiation. The light produced by the scintillator layer in response to incoming radiation undergoes photoelectric conversion through the photodiode to produce an electric charge, which is stored in the capacitor, and the electric charge stored in the capacitor is read out through the TFT as an electric signal.

The detector carrier 28 moves the FPD 24 in the same direction indicated by the arrow x as the radiation carrier 26.

Like the radiation carrier 26, the detector carrier 28 may be any known carrier for the FPD used in radiographic imaging systems capable of long region imaging.

As described above, the imaging system 10 is also capable of long region imaging in addition to normal imaging whereby the examinee H, who stays stationary, is imaged once by a single exposure.

Long region imaging is an imaging method whereby the radiation exposure field and the radiation detector 24 are moved along the body axis of the examinee H, who stays motionless, to take a plurality of images of a region such as the whole region of a spine or the whole region of lower extremities that is longer than the imaging surface of the radiation detector 24, whereupon these images are combined to produce a radiographic image of the long region.

When performing long region imaging with the imaging system 10, association control means 48 of control means 40 described later effects control such that the radiation source carrier 26 and the detector carrier 28 intermittently transfer the radiation source 20 and the FPD 24 synchronously with each other in the direction indicated by the arrow x and stop them to take a radiographic image in the respective stop positions.

Suppose, for examples, that the transfer is carried out intermittently, stopping in three positions indicated by solid lines and dashed-dotted lines in FIG. 1. When the radiation source carrier 26 and the detector carrier 28 stop the transfer, the radiation source 20 emits radiation (effects exposure), and the FPD 24 detects the radiation that has penetrated to produce an image signal for a radiographic image of the examinee H. Hereinafter, an image obtained by a single imaging in long region imaging will be called a "short image" for the sake of simplicity. In long region imaging, the number of times short images are taken, the positions in which short images are taken, and other conditions are set by progress managing means 50 of control means 40 described later.

The image signal produced by the FPD 24 is read out at a given timing by signal processing means (image data receiving means) 32. Short images are combined by image processing means 34 to produce a long radiographic image of the whole lower extremities or the whole spine, for example. In long region imaging, the positions in which short images are taken, the number of times short images are taken, and other conditions are set by the control means 40 according to an imaging region entered at an operation panel 42.

A scheme involving these steps will be described later in detail.

In the imaging system 10 of the invention, not only such a long region imaging but also various other imaging methods may be used to implement an imaging method whereby a plurality of images are successively taken of (or imaging is performed successively by scanning) an examinee holding still during an imaging session by changing the imaging position (imaging region) and the imaging angle (radiation emission angle).

Examples thereof include said tomosynthesis imaging, observation of movements based upon a plurality of radiographic images representing movements of a part of interest of an examinee such as a motion image representing a chest in motion caused by respiration (JP 2004-410 A), and energy subtraction whereby a radiographic image is taken by a single radiography using a plurality of different radiographic energies and differences are found, among other processing, to produce an image from which soft tissues and other unnecessary parts have been removed (JP 2002-325756 A).

Note that normal imaging by the imaging system 10 of the invention may be performed in the same manner as by known radiographic imaging systems capable of long region imaging.

The data processing/output unit 14 processes the image signal of an image produced by the FPD 24 and outputs a radiographic image thereof; it comprises signal processing means 32, image processing means 34, a monitor 36, and a printer 38.

A radiographic image signal produced by the FPD 24 is read out by the signal processing means 32 a given length of time (accumulation time) after exposure.

The signal processing means 32 performs analog-to-digital conversion, logarithm conversion, etc., on the image signal read out from the FPD 24 to output a digital image data to the image processing means 34.

The image processing means 34 performs given image processing such as offset correction, residual image correction, tone correction/density correction and sharpness correction on the image data processed by the signal processing means 32 and transmits image data to the monitor 36 and the printer 38 for output. Further, the image processing means 34 performs image processing and image synthesis of short images in long region imaging to produce and output a long radiographic image to the monitor 36 and the printer 38.

The image processing and image synthesis of short images in the image processing means 34 may be performed each by known methods.

In long region imaging, the image processing means 34 performs said image processing on each short image separately to output the thus processed image data to the monitor 36 as preview image data, whereupon the monitor 36 displays a preview image of each short image.

Each time a preview image of each short image is outputted to the monitor 36, the image processing means 34 outputs a signal to the progress managing means 50 of the control means 40 to indicate that a short image has been taken. Thus, the progress managing means 50 detects the progress of long region imaging as will be described later.

The monitor 36 is a known monitor (display) to receive image data from the image processing means 34 and display an image.

The printer 38 is also a known printer to receive an image from the image processing means 34 and produce a print.

The control unit 16 performs operation and control of the imaging system 10 and comprises control means 40, an operation panel 42, and progress notification means 46.

In the imaging system 10, the control means 40 of the control unit 16 and the signal processing means 32 and the image processing means 34 of the data processing/output unit 14 are constructed typically using a computer or a workstation. Therefore, at least part of these components may be constructed integrally.

The operation panel 42 is provided to operate the imaging system 10 and comprises an imaging switch, menu setting means, mode setting means, and imaging condition inputting means.

The imaging switch is provided to effect radiography. In one example thereof, when the imaging switch is depressed to its first step, the system stands by for imaging; when the imaging switch is depressed to its second step, imaging starts.

The menu setting means sets an imaging menu including an imaging region such as a chest, an abdomen, the whole lower extremities, and the whole spine and a mode of imaging such as normal imaging and long region imaging.

The mode setting means is provided to select one of an automatic mode in which the system automatically sets imaging conditions and a manual mode in which the operator (radiologist, medical doctor, etc.) sets imaging conditions.

The imaging condition inputting means is provided to input imaging conditions for taking a radiographic image such as imaging range, tube voltage, and exposure time.

These means may be materialized using any known means used in radiographic imaging systems.

The control means 40 performs operation and control of the units of the imaging system 10 such as the imaging unit 12 and the data processing/output unit 14. The units of the imaging system 10 operate basically in response to a control signal from the control means 40.

Figure 2:
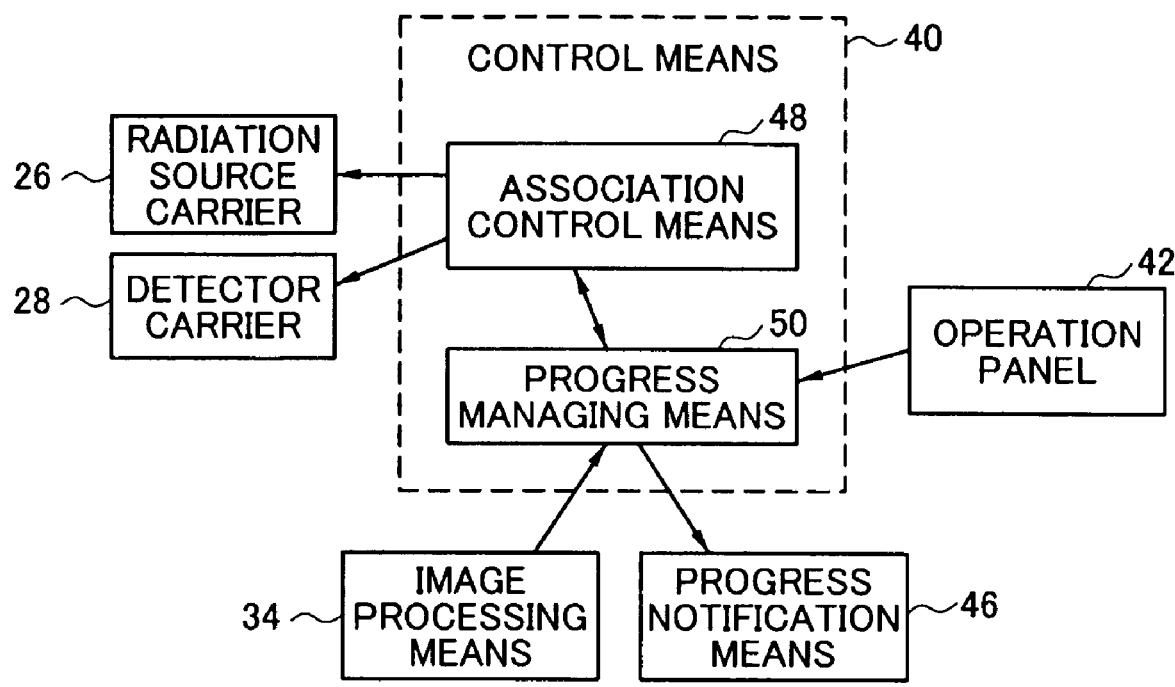
FIG. 2 is a block diagram illustrating control means used in the embodiment.

As illustrated in FIG. 2, the control means 40 of the imaging system 10 comprises association control means 48 and the progress managing means 50.

The association control means 48 controls the operation of the radiation source carrier 26 and the detector carrier 28 in an imaging session in such a manner that the radiation source 20 and the FPD 24 are located in appropriate synchronism in their respective appropriate positions corresponding to their imaging positions (imaging positions for taking short images in long region imaging and an imaging position in normal imaging).

Alternatively, instead of moving both of the radiation source 20 and the FPD 24, one may use a radiation source capable of irradiating the whole region to be covered thereby to achieve long region imaging just by moving the radiation detector. Conversely, one may use a radiation detector covering the whole region to be imaged to achieve long region imaging just by moving the radiation source.

The progress managing means 50 sets a number of radiographic images into which a long image is divided in long region imaging, imaging positions for taking short images, positions of the radiation source 20 and the FPD 24 for taking short images, and the like according to the imaging menu and the imaging range (imaging region) set at the operation panel 42.

Further, the progress managing means 50 manages the progress of long region imaging including transfer of the radiation source 20 and the FPD 24, initiation and termination of the imaging session of each short image, imaging time, elapsed time from the start of long region imaging, a length of time it takes to complete long region imaging, and the termination of long region imaging.

As described above, each time the image processing means 34 performs image processing on a short image and outputs a preview image data to the monitor 36, the image processing means 34 supplies a termination signal to that effect to the progress managing means 50. Upon receiving the termination signal, the progress managing means 50 knows the progress of the long region imaging and effects management of the progress of the long region imaging.

Further, upon receiving the termination signal from the image processing means 34, the progress managing means 50 produces and outputs long region imaging progress information to the progress notification means 46.

Upon receiving the long region imaging progress information from the progress managing means 50, the progress notification means 46 notifies the examinee H of the progress of the long region imaging.

The progress notification means 46 may be any means, provided that it allows the examinee H to know the progress of long region imaging, examples thereof including display means, light emission means such as an LED or LEDs, or an indicator located in a position where any of these means can be seen by the examinee H lying on the imaging table 22, sound output means disposed in an imaging room or attached to the imaging table 22, vibration generating means disposed in a position where it is in contact with the examinee H lying on the imaging table 22, vibration generating means held by the examinee H lying on the imaging table 22, and illumination control means for controlling the illumination in the imaging room.

The progress notification means 46 may be a combination of two or more of these means.

The long region imaging progress information of which the progress notification means 46 notifies the examinee H, i.e., the long region imaging progress information produced by the progress managing means 50, is not limited specifically and may be a variety of information.

The long region imaging progress information may, for example, be a scheduled number of images to be taken, termination of the imaging session of each image, the number of images so far taken, the number of images yet to be taken, a scheduled number of images to be taken together with the number of images so far taken and/or the number of images yet to be taken, the remaining imaging time, a scheduled imaging time together with the elapsed time and/or the remaining imaging time, the ratio of the number of images so far taken to a scheduled number of images to be taken, the ratio of the elapsed time to a scheduled imaging time, and termination of long region imaging. Note that the numbers of images referred to in the above examples are all those of short images.

The imaging progress information given to the examinee may of course be composed of different kinds of information such as the number of images yet to be taken and the remaining imaging time.

Where vibration generating means such as a vibrator is used as the progress notification means 46, the examinee H may be notified of the progress of the long region imaging through the vibrator switched on and off and variation in vibration intensity and frequency of vibration generation, and the like. Where light emission means such as an LED is used as the progress notification means 46, the examinee H may be notified of the progress of the long region imaging through the LED switched on and off and variation in flashing frequency, the number of LEDs turned on, amount of light, and color of light, and the like.

Where the output of sound is used as the progress notification means 46, a signal sound such as a beep may be produced aside from a voice articulated in specific words. In this case, the examinee H may be notified of the progress of the long region imaging by way of the number of times sound is generated, the frequency with which the signal sound is generated, variation in sound volume, sound quality, and sound pitch, and the like.

Use of adjustment of the illumination in the imaging room as the progress notification means 46 is preferable because an anxiety the examinee H may feel can be lessened in a desirable manner. In a typical imaging room for taking a radiographic image, illumination is held to a low level to make a radiation exposure field recognition light easier to see. Thus, when a series of images are successively taken as in long region imaging, the examinee H is required to remain motionless in a dark room and wait therein for the termination of imaging session, which causes anxiety to a number of individuals.

When the examinee H, however, is notified of the progress of long region imaging by using the adjustment of the illumination in the imaging room, the examinee H can not only know the progress of the long region imaging but also his/her anxiety can be greatly lessened. The adjustment of the illumination may be achieved in such a manner that, for example, the amount of light is increased progressively or gradually according to the progress of the imaging session, and that the brightness in the imaging room is increased upon termination of the imaging session.

Now, the operations of long region imaging achieved by the imaging system 10 will be described referring to FIGS. 1 and 2.

First, an imaging menu and an imaging mode are selected at the operation panel 42, followed by input of imaging conditions such as a tube voltage and an imaging range for long region imaging.

Such information inputted from the operation panel 42 is supplied to the progress managing means 50 of the control means 40. The progress managing means 50 sets a number of times short images are to be taken, imaging positions in which the short images are respectively taken, positions in which the radiation source 20 and the FPD 24 are located for taking short images, and the like according to the supplied information and transmits necessary information to the corresponding units such as the association control means 48.

Further, the progress managing means 50 produces given information on the progress of long region imaging such as a scheduled number of images to be taken and a scheduled imaging time and supplies such information to the progress notification means 46 as required. Thereon, the progress notification means 46 notifies the examinee H of information such as the scheduled number of images to be taken and the scheduled imaging time.

When the imaging button on the operation panel 42 is depressed to its first step, the system stands by for imaging in such a manner that the association control means 48, for example, instructs the radiation carrier 26 and the detector carrier 28 to transfer the radiation source 20 and the FPD 24 to the respective imaging positions for taking a first image.

When the system is ready for imaging and the imaging button is depressed to its second step, long region imaging starts as the radiation source 20 emits radiation with a given tube voltage for a preset time period, and the radiation having penetrated the examinee H enters the FPD 24.

When a given time (accumulation time) has elapsed after termination of emission of radiation, the signal processing means 32 reads out an image signal from the FPD 24, performs given processing thereon such as analog-to-digital conversion and logarithm conversion, and outputs image data for a first short image to the image processing means 34.

The image processing means 34 performs given image processing such as offset correction and sharpness correction on the supplied image data and outputs image data thus processed to the monitor 36 as preview image data for the first short image. The monitor 36 displays the preview image. Upon outputting the preview image data for the first short image to the monitor 36, the image processing means 34 outputs a termination signal to that effect to the progress managing means 50.

Upon receiving the termination signal for the first short image from the image processing means 34, the progress managing means 50 knows the termination of imaging session for taking the first image in the long region imaging, and produces information on the progress of the long region imaging to the effect, for example, that "A first of a total of scheduled X images has just been taken," "Y images now remain to be taken," or "Imaging session ends in Z seconds" and outputs such information to the progress notification means 46. The progress notification means 46 outputs such imaging progress information through sound, image display, etc. to notify the examinee H of the progress of long region imaging.

When the radiation exposure for the first image is terminated, the association control means 48 instructs the radiation source carrier 26 and the detector carrier 28 to move the radiation source 20 and the FPD 24 to the respective imaging positions for taking a second short image along with some other operations such as said signal processing.

When the preparations for taking a second short image such as the transfer of the FPD 24 are completed, the radiation source 20 likewise irradiates the examinee H, and the radiation that has penetrated the examinee H enters the FPD 24.

When a given time has elapsed after irradiation, the signal processing means 32 reads out an image signal from the FPD 24, performs given processing, and outputs image data for a second short image to the image processing means 34. The image processing means 34 performs image processing on the image data and outputs the thus processed image data to the monitor 36 as preview image data for the second short image, whereupon the monitor 36 displays the preview image of the second short image.

Upon outputting the preview image data to the monitor 36, the image processing means 34 outputs a termination signal to that effect to the progress managing means 50. Upon receiving the termination signal for the second short image from the image processing means 34, the progress managing means 50 knows the termination of imaging session for taking the second image in the long region imaging, and produces information on the progress of the long region imaging to the effect, for example, that "A second image of a total of scheduled X images has just been taken" and outputs such information to the progress notification means 46. Thereon, the progress notification means 46 notifies the examinee H of the progress of the imaging session by outputting information thereon through sound, a displayed image, etc.

Upon termination of exposure of the second short image, the association control means 48 likewise instructs the radiation source carrier 26 and the detector carrier 28 to transfer the radiation source 20 and the FPD 24 to the respective imaging positions for taking a third short image, whereupon a third short image is taken and processed, a preview image thereof is displayed, and the examinee H is notified of the progress of the imaging session when the third short image has been taken, thus likewise repeating the same procedure such that short images are taken, preview images are displayed and the examinee H is notified of the progress of the imaging session for a fourth image, a fifth image and onward until a scheduled number of short images have all been taken.

When a scheduled number of short images have been all taken, the progress managing means 50 produces information, which may be worded as, for example, "Images have all been taken," to indicate that long region imaging has been completed, and supplies the information to the progress notification means 48, which in turn outputs the information through sound, display, etc. to notify the examinee H of the termination of the imaging session. More preferably, the progress managing means 50 instructs the progress notification means 48 to increase the brightness of the imaging room upon termination of the long region imaging, whereupon the progress notification means 48 controls imaging room illumination adjusting means to increase the illumination, i.e., the brightness inside the imaging room.

Concurrently, the image processing means 34 combines the short images in hand to produce and output a long radiographic image data to the monitor 36 and/or the printer 38 to display the long image on the monitor 36 and/or produce a print thereof through the printer 38.

As will be apparent from the foregoing description, the present invention allows the examinee H to know the length of time for taking images, the progress of the imaging session, the time that remains to complete the imaging session, the number of images so far taken or yet to be taken, and the like in a typically time-consuming long region imaging (an imaging session where a series of images are taken successively).

According to the present invention, therefore, a psychological burden on the part of the examinee H can be greatly lessened in long region imaging where the examinee H was conventionally not allowed to know when the imaging session would end, and required to hold still patiently during the imaging session.

In the imaging system 10, the progress managing means 50 knows the progress of the long region imaging as it acquires output information from the image processing means 34 to the effect that the preview image data has been outputted. The invention is not limited thereto, however. The progress managing means 50 may be adapted to know the progress of the imaging session by any of various other methods.

For example, the progress managing means 50 may know the progress of the long region imaging when relevant units supply the progress managing means 50 with such information as, for example, information on irradiation by the radiation source 20, information that the FPD 24 has been exposed to radiation exceeding a threshold, information that the signal processing means 32 has read out an image signal from the FPD 24, information that the monitor 38 has displayed a preview image, and information that sensors disposed in appropriate locations in the imaging table 22 have received radiation. Alternatively, the progress managing means 50 may know the progress of the long region imaging by observing the operations and the like of the relevant units and detecting information exemplified above (including information that the image processing means 34 has outputted preview image data).

Further, the progress detection means and the progress notification means in the radiographic imaging system of the invention are not to be construed to operate solely in cases such as long region imaging and tomosynthesis imaging, where a series of images are successively taken. In normal imaging, for example, the progress of the imaging session may be detected by the progress detection means, and an examinee may be notified of the detection results.

While the radiographic imaging system of the present invention has been described above in detail, it is to be understood that the invention is not limited to the above embodiment and various changes and modifications may be made without departing from the true spirit and scope of the invention.

What is claimed is:

1. A radiographic imaging system for successively taking a series of images, comprising:
   a radiation source for irradiating an examinee with radiation;
   a radiation detector for detecting radiation that has penetrated the examinee to acquire radiographic image data;
   image data receiving means for receiving the radiographic image data from the radiation detector and outputting a termination signal indicating that an image has been taken each time receiving the radiographic image data;
   association control means for controlling operations of the radiation source and the radiation detector;
   progress managing means for receiving the termination signal from the image data receiving means to detect a progress of an imaging session for successively taking a series of images based on the received termination signal; and
   progress notification means for notifying the examinee of a progress of imaging session detected by the progress managing means.

2. The radiographic imaging system according to claim 1, wherein the progress notification means notifies the examinee of the progress of imaging session through sound output.

3. The radiographic imaging system according to claim 1, wherein the progress notification means notifies the examinee of the progress of imaging session through image display.

4. The radiographic imaging system according to claim 1, wherein imaging by the radiographic imaging system is performed in an imaging room, the progress notification means notifying the examinee of the progress of imaging session through adjusting an illumination in the imaging room.

5. The radiographic imaging system according to claim 1, further comprising:
   an operation panel for inputting imaging conditions for successively taking the series of images,
   the progress managing means calculating at least one of a number of images to be taken and an imaging time for successively taking the series of images.

6. The radiographic imaging system according to claim 5, wherein the progress notification means notifies the examinee of a remaining number of images to be taken out of the series of images as information on the progress of imaging session.

7. The radiographic imaging system according to claim 5, wherein the progress notification means notifies of a remaining imaging time in the imaging session for taking the series of images as information on the progress of imaging session.

8. The radiographic imaging system according to claim 1, further comprising: at least one of
   a radiation carrier for moving the radiation source in a given direction; and
   a detector carrier for moving the radiation detector in the given direction,
   the association control means causing at least one of the radiation carrier and the detector carrier to move at least one of the radiation source and the radiation detector to a plurality of imaging positions, where the series of images are taken.

* * * * *